United States Patent [19]
Strand et al.

[11] Patent Number: 5,141,324
[45] Date of Patent: Aug. 25, 1992

[54] VISUAL MONITORING DEVICE FOR SLUDGE CONDITIONING SYSTEM

[75] Inventors: Frank L. Strand, Bourbonnais, Ill.; Thomas P. Keyes, Pinehurst, Tex.

[73] Assignee: Stranco, Inc., Bradley, Ill.

[21] Appl. No.: 634,017

[22] Filed: Dec. 26, 1990

[51] Int. Cl.⁵ .......................................... G01N 21/85
[52] U.S. Cl. ..................... 356/441; 356/23; 116/276; 73/861.05
[58] Field of Search ............. 356/441, 432, 23; 138/104; 116/264, 276; 73/861.05

[56] References Cited

U.S. PATENT DOCUMENTS

| | | | |
|---|---|---|---|
| 2,620,385 | 12/1952 | Grant | 356/441 |
| 2,624,308 | 1/1953 | Wittlin | 138/104 |
| 4,487,075 | 12/1984 | Karidis | 73/861.05 |

*Primary Examiner*—Vincent P. McGraw
*Assistant Examiner*—LaCharles P. Keesee
*Attorney, Agent, or Firm*—Emrich & Dithmar

[57] ABSTRACT

The visual monitoring apparatus includes a transparent tube section with coupling flanges at each end for coupling to adjacent conduit sections carrying a stream of conditioned sludge which includes agglomerated solid bodies. Control rods extend between the coupling flanges to strengthen the tube. A strobe light is mounted in a housing which is mountable alongside the tube and closely conforms to the shape thereof for confining the strobe light to a predetermined area of the tube and isolating that area from ambient light. The housing accommodates the control rods therethrough and contains a mirror which directs light reflected from the illuminated contents of the tube along a viewing path through a view port in the housing which is closed by a door or hatch. The frequency of the strobe can be adjusted to correspond to the flow rate of the fluid in the tube for creating the visual impression of substantially stopping the movement of the solid bodies in the tube.

17 Claims, 1 Drawing Sheet

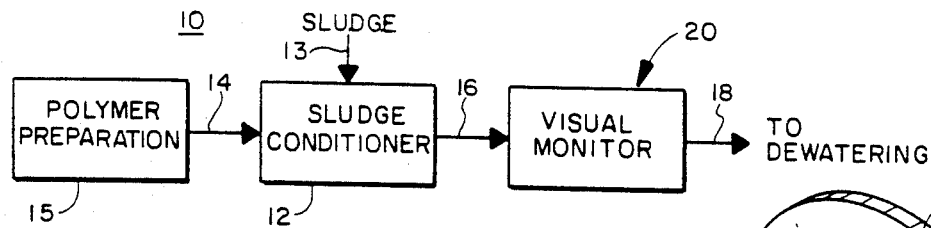
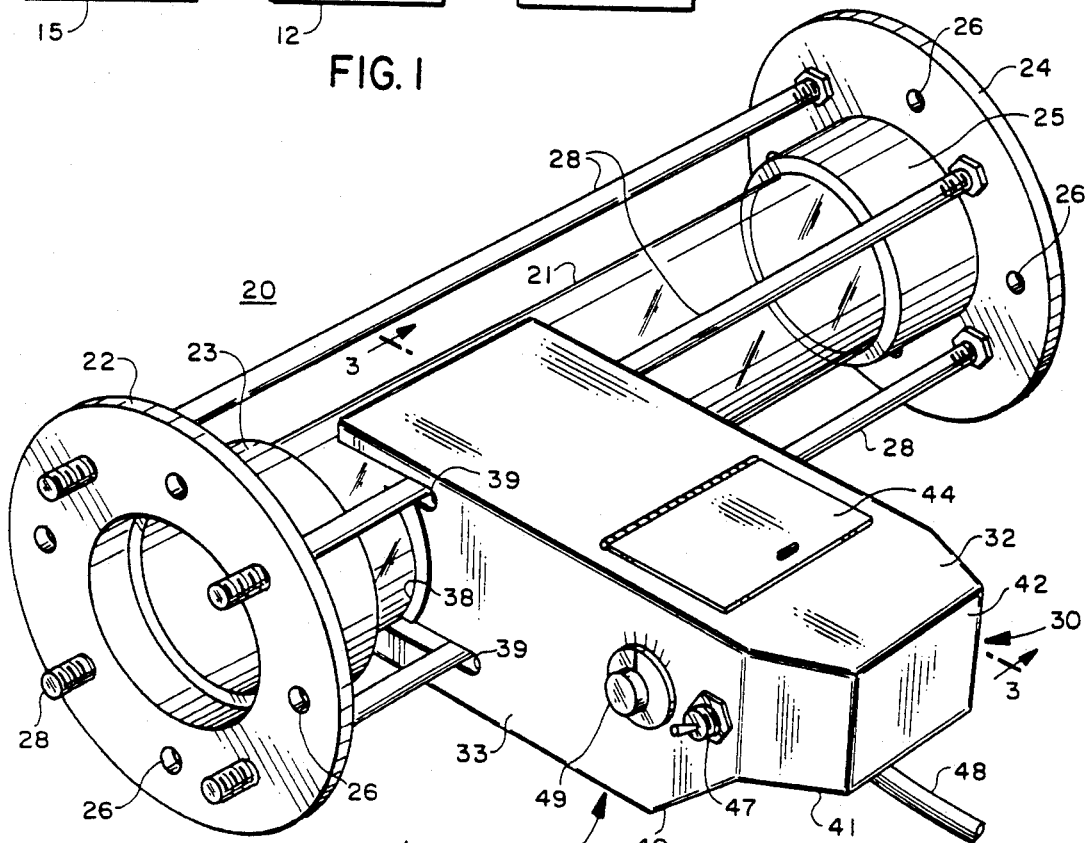
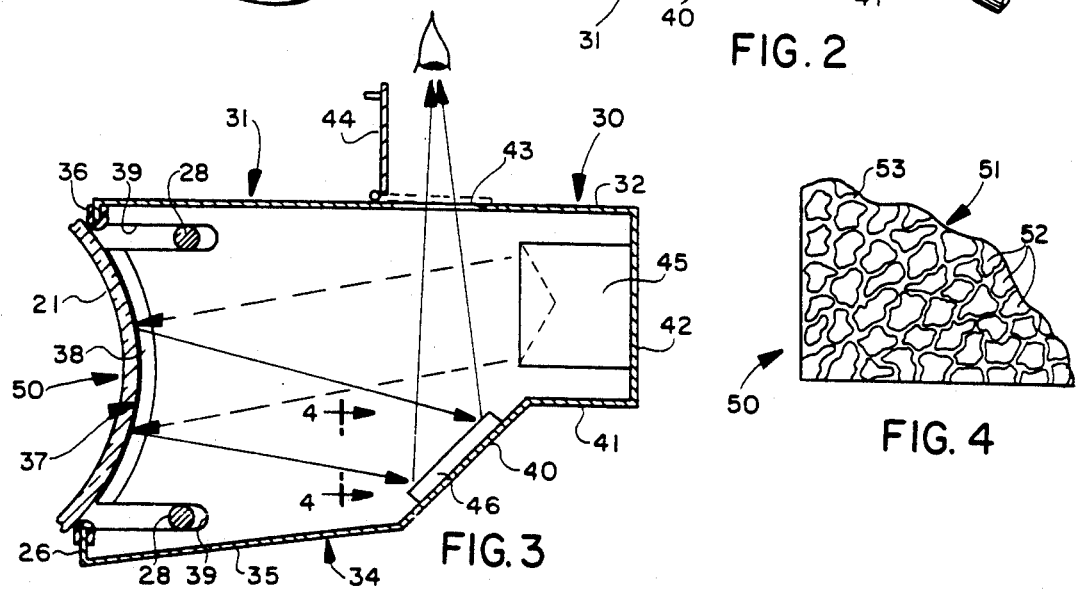

VISUAL MONITORING DEVICE FOR SLUDGE CONDITIONING SYSTEM

BACKGROUND OF THE INVENTION

1. Field of the Invention

The present invention relates to systems for carrying solid bodies entrained in a fluid stream, and has particular application to sludge treatment systems.

2. Description of the Prior Art

In waste water treatment systems it is common to pass the waste water through a settling or sedimentation process to permit solid materials to settle out of the water and form sludge, which consists of fine particulate solids in suspension. Since the sludge has a high water content, before the solid material therein can be effectively disposed of, substantially all of the water must be removed therefrom in a dewatering apparatus, such as a centrifuge or a filter press. In order for the dewatering apparatus to work most efficiently, the solid material must be in the form of solid particles or bodies of a particular size, which is typically substantially greater than the size of the particles as they come from the settling or sedimentation process.

Accordingly, the sludge is first conditioned by mixing it with a flocculent, such as a polyelectrolyte, which causes the solid particles to agglomerate or clump together to form what is known as "floc". The size of the floc clumps or bodies is a function of the mixing energy applied in the conditioning apparatus which mixes the sludge with the flocculent. Heretofore, system operators have determined whether or not the floc is of the proper size by simply visually observing it as it enters the dewatering apparatus. This has several drawbacks. First of all, in some applications it is necessary to view a moving stream of conditioned sludge which makes it difficult to accurately gauge the size of the floc. Furthermore, in some applications it is not possible to view the conditioned sludge as it enters the dewatering apparatus.

Also, the floc size is partly a function of turbulence which the conditioned sludge stream undergoes as it passes from the outlet of the sludge conditioning apparatus to the dewatering apparatus. Thus, it is a function of the piping system design, which may include a number of elbows, valves or the like which introduce substantial turbulence. Such turbulence can subject the floc to high shear forces which may break up the floc particles and thereby partially destroy the effect of the sludge conditioning process. Accordingly, what the viewer sees entering the dewatering apparatus may be quite different from what is produced by the sludge conditioning apparatus and if the floc entering the dewatering apparatus is unacceptable, it may be very difficult to determine whether the problem lies in the piping system design or in the amount of energy imparted in the sludge conditioning apparatus.

SUMMARY OF THE INVENTION

It is a general object of this invention to provide an improved sludge conditioning system and, in particular, an apparatus for monitoring the condition of solid bodies entrained in a fluid stream, which avoids the disadvantages of prior systems and apparatus while affording additional structural and operating advantages.

An important feature of the invention is the provision of a visual monitoring apparatus which permits accurate viewing and monitoring of solid bodies entrained in a moving fluid stream.

In connection with the foregoing feature, it is another feature of the invention to provide an apparatus of the type set forth, which creates the visual effect of substantially stopping the motion of the solid bodies.

Another feature of the invention is the provision of an apparatus of the type set forth, which permits inspection of the solid bodies while the fluid stream is moving through a conduit.

In connection with the foregoing feature, it is another feature of the invention to provide an apparatus of the type set forth, which can be used at any desired location in a conduit network.

These and other features of the invention are attained by providing visual monitoring apparatus for viewing solid bodies entrained in a fluid stream comprising: a tube adapted to receive the fluid stream therethrough, the tube having a light-transmitting wall portion, stroboscopic illumination means generating periodic light flashes at a predetermined rate, the illumination means including means directing the light flashes to the tube for illuminating the contents of the tube through the light-transmitting wall portion, and viewing means for viewing the illuminated contents of the tube.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1 is a functional block diagram of a sludge treatment system incorporating a visual monitoring device constructed in accordance with and embodying the features of the present invention;

FIG. 2 is a perspective view of the visual monitoring device of the present invention;

FIG. 3 is a view in vertical section taken along the line 3—3 in FIG. 2; and

FIG. 4 is an enlarged, fragmentary view taken along the line 4—4 in FIG. 3 and illustrating a portion of the viewing window defined by the present invention showing sludge floc particles as viewed by a user.

DESCRIPTION OF THE PREFERRED EMBODIMENT

Referring to FIG. 1, there is illustrated a sludge treatment system generally designated by the numeral 10, which includes a sludge conditioner device 12 for receiving sludge at an inlet conduit 13 from an associated sludge-producing process, such as a settling or sedimentation process. The sludge conditioner device 12 mixes the sludge with a prepared flocculent, such as a polymer or polyelectrolyte, received at an inlet conduit 14 from a polymer preparation apparatus 15. The sludge conditioner device 12 preferably includes a chamber containing a paddle-wheel impeller (not shown), and into which the sludge and flocculent are introduced for mixing together by the impeller. Typically, the sludge conditioner device 10 will be provided with a control to selectively vary the speed of the impeller, thereby to vary the energy input to the mixture. The sludge conditioner device may be of the type sold by Stranco, Inc. under the trademark "OPTIFLOC", while the polymer preparation apparatus 15 may be of the type sold by Stranco, Inc. under the trademark "POLYBLEND". The conditioned sludge exits the sludge conditioner device 12 through an outlet conduit 16 for transfer to an inlet 18 to associated dewatering apparatus (not shown), which may be of any desired type, such as a centrifuge or a filter press, for removing free water from the conditioned sludge.

The visual monitoring device 20 of the present invention is coupled between the outlet conduit 16 from the sludge conditioner device 12 and the inlet 18 to the dewatering apparatus. Referring to FIGS. 2 and 3, the visual monitoring device 20 includes an elongated tube 21 which is circularly cylindrical in shape and is formed of a material which is transparent to visible light, such as a suitable acrylic. The tube 21 is provided with an inlet coupling flange 22 at one end thereof, which has a cylindrical collar 23 disposed in coaxial surrounding relationship with the adjacent end of the tube 21. Similarly, an outlet coupling flange 24 is provided having a cylindrical collar 25 which coaxially receives the other end of the tube 21. The flange collars 23 and 25 are fixedly secured to the adjacent ends of the tube 21 in fluid-tight relationship by suitable means.

Each of the flanges 22 and 24 is provided with a plurality of bolt holes 26 for receiving therethrough complementary bolts (not shown) for coupling the flanges 22 and 24 to similar flanges on adjacent conduit sections in a known manner. Interconnecting the coupling flanges 22 and 24 are a plurality of elongated control rods 28, which may be formed of steel and are provided with externally threaded ends which are received through complementary openings in the coupling flanges 22 and 24 and through like openings in the mating flanges of the adjacent conduit sections (not shown) for cooperation with associated nuts (not shown). The control rods 28 serve to strengthen and rigidify the tube 21. The control rods 28 may be four in number and are preferably equiangularly spaced apart around the tube 21.

The visual monitoring device 20 also includes a strobe assembly 30 which has a box-like housing 31 having a top wall 32, depending side walls 33 and a bottom wall 34 which includes a gradually sloping front portion 35. The front edges of the walls 32-35 are joined by a front wall 36 which has a window 37 cut therefrom, which joins arcuate cutouts 38 in the side walls 33, thus to provide a generally semi-cylindrical recess or opening in the front of the housing 31 which is mateable with one side of the tube 21. Preferably, the side walls 32 are also provided with slots 39 for accommodating passage of the control rods 39 therethrough. The bottom wall 34 also has a more steeply sloped mid portion 40 and a rear portion 41 which is substantially parallel with the top wall 32. Thus, the rear end of the housing 31 is smaller than the front end thereof and is closed by a rear wall 42. Formed in the top wall 32 of the housing 31 is a generally rectangular view port 43 which is closed by a hinged cover 44 for movement between open and closed positions, respectively illustrated in solid and broken line in FIG. 3.

Mounted within the small rear end of the housing 31 is a strobe lamp 45 which provides intermittent periodic flashes of light in a known manner. The light from the lamp 45 is directed forwardly through the front of the housing 31, as indicated by the broken line arrows in FIG. 3, for illuminating the portion of the tube 21 which is confined or framed by the front end of the housing 31, and thereby illuminating the contents of the tube 21 which lie along the inside of the framed portion thereof. Mounted within the housing 31 along the sloping mid portion 40 of the bottom wall 34 is a rectangular mirror 46 which may have, e.g., an area of approximately ten square inches and which is inclined at an angle so as to direct light reflected from the illuminated contents of the tube 21 along a line of sight upwardly through the view port 43, as indicated by the solid line arrows in FIG. 3, so as to be viewable by a user when the cover 44 is open. The strobe assembly 30 includes an ON/OFF switch 47 for energizing the lamp 45, a power cord 48 for coupling to an associated source of power, such as a 120 VAC source, and a frequency control 49 for selectively varying the frequency of the light flashes emanating from the strobe lamp 45.

In use, the housing 31 is mounted closely adjacent to the tube 21 so that the front wall 36 and the side walls 33 engage the tube 21 to frame and direct the light from the strobe lamp 45 onto a designated portion of the tube 21 and to prevent the admission of ambient light to that framed portion. The strobe assembly 30 may be mounted adjacent to the tube 21 by any suitable means (not shown). For example, suitable brackets (not shown) could be provided for mounting the strobe assembly 30 to the coupling flange bolts, in which case the strobe assembly 30 would be disposed closely adjacent to either one of the coupling flanges 22 or 24.

The portion of the tube 21 which may be viewed via the view port 43 and the mirror 46 is designated 50. Typically, the tube 21 will be filled with conditioned sludge which is traveling therethrough from left to right, as viewed in FIG. 2, in a generally spiral motion. The conditioned sludge consists of relatively densely packed floc, which comprises agglomerated bodies of solids 52 entrained in a stream of free water 53 (see FIG. 4). The bodies 52 are of irregular shape and preferably of generally the same size, each consisting of polyelectrolyte flocculent and solid sludge material agglomerated thereto. The size of the bodies 52 may vary inversely with the energy imparted by the sludge conditioner device 12. In a typical application, the size of the bodies 52 may vary in size from approximately 1/32 inch to approximately 5/16 inch. The operator of the system 10 must monitor the size of the bodies 52 so that they are maintained at an optimum size for the most efficient operation of the associated dewatering apparatus.

When it is desired to view the contents of the tube 21, the strobe lamp 45 is energized and its periodic flashing frequency is adjusted by the frequency control 49 to a rate which corresponds to the flow rate of the conditioned sludge through the tube 21. The result is to create the visual effect of substantially stopping the motion of the illuminated ones of the agglomerated bodies of solids 52, as illustrated in FIG. 4, so that they can clearly viewed by the user and their size can be relatively accurately determined. If the size is incorrect, the operator can adjust the speed of the impeller in the sludge conditioner device 12 accordingly until the proper size is achieved. Furthermore, it will be appreciated that the user can, by the use of the visual monitoring device 20, compare the size of the agglomerated bodies of solids 52 at the outlet of the sludge conditioner device 12 with the size of those bodies as they enter the dewatering apparatus. In this way, the user can determine what effect the piping between the visual monitoring device 20 and the dewatering apparatus is having on the size of the floc.

From the foregoing, it can be seen that there has been provided an improved visual monitoring apparatus which provides effective monitoring of the size of solid bodies entrained in a moving fluid stream while the stream is confined in a conduit.

We claim:

1. Visual monitoring apparatus for viewing solid bodies entrained in a fluid stream flowing at a predetermined rate comprising: a tube adapted to receive the fluid stream therethrough, said tube having a light-transmitting wall portion, stroboscopic illumination means generating periodic light flashes at a predetermined rate corresponding to said flow rate, said illumination means including means directing the light flashes to said tube for illuminating the contents of said tube through said light-transmitting wall portion, said directing means including confinement means for limiting the illumination to a predetermined area of said tube, said confinement means including means for shielding said predetermined area of said wall portion from ambient light, and viewing means for viewing the illuminated contents of said tube.

2. The apparatus of claim 1, wherein said tube is circularly cylindrical.

3. The apparatus of claim 1, wherein said wall portion is transparent to visible light.

4. The apparatus of claim 1, wherein said tube is entirely formed of a light-transmitting material.

5. The apparatus of claim 1, wherein said viewing means includes a mirror disposed within said confinement means for directing light reflected from the illuminated contents of said tube along a line of sight, and door means and in said confinement means along said line of sight for permitting viewing of the illuminated contents of said tube.

6. The apparatus of claim 1, and further comprising means for selectively varying the flashing rate of said illumination means.

7. In a sludge treatment system including a sludge conditioner for mixing sludge with a flocculent to produce at its output conditioned sludge consisting of agglomerations of solids entrained in a fluid stream flowing at a predetermined flow rate, the improvement comprising: a tubular section connected to the outlet of the sludge conditioner, said tubular section having a light-transmitting wall portion, stroboscopic illumination means generating periodic light flashes at a predetermined rate corresponding to said flow rate, said illumination means including means directing the light flashes to said tubular section for illuminating the agglomerations of solids in said tubular section through said light-transmitting wall portion, and viewing means for viewing the illuminated agglomerations of solids, said viewing means including a mirror disposed for directing light reflected from the illuminated agglomerations of solids along a predetermined viewing path.

8. The system of claim 7, wherein said wall portion is transparent to visible light.

9. The system of claim 8, wherein said wall portion includes the entirety of said tubular section.

10. The system of claim 7, wherein said directing means includes confinement means for limiting the illumination to a predetermined area of said wall portion.

11. The system of claim 10, wherein said confinement means includes means for shielding said predetermined area of said wall portion from ambient light.

12. The system of claim 7, and further comprising means for selectively varying the flashing rate of said illumination means.

13. Visual monitoring apparatus for viewing solid bodies entrained in a fluid stream flowing at a predetermined flow rate comprising: a tube adapted to receive fluid stream therethrough, said tube having a light-transmitting wall portion, two coupling structures respectively connected to the opposite ends of said tube for coupling thereof to adjacent conduit structures, means interconnecting said coupling structures for strengthening said tube, stroboscopic illumination means generating periodic light flashes at a predetermined rate corresponding to said flow rate, said illumination means including means directing the light flashes to said tube for illuminating the contents of said tube through said light-transmitting wall portion, said directing means including housing means for confining the illumination thereby to a predetermined area of said wall portion, said housing means including means accommodating passage of said interconnecting means therethrough, and viewing means for viewing the illuminated contents of said tube.

14. The apparatus of claim 13, wherein said housing means includes means substantially conforming to the external shape of said tube.

15. The apparatus of claim 13, wherein said illumination means includes a stroboscopic light source disposed within said housing.

16. The apparatus of claim 13, wherein said viewing means includes a mirror disposed within said housing for directing light reflected from the illuminated contents of said tube along a predetermined viewing path.

17. The apparatus of claim 16, wherein said housing includes a door disposed along said viewing path and movable between open and closed conditions for permitting viewing of the illuminated contents of said tube.

* * * * *